United States Patent [19]

Bowen et al.

[11] Patent Number: 4,752,444
[45] Date of Patent: Jun. 21, 1988

[54] METHOD FOR STERILIZING A DENTAL HANDPIECE

[75] Inventors: Stanley A. Bowen, Santa Ana; William L. Henderson, Stanton, both of Calif.

[73] Assignee: Bowen Ltd., Santa Ana, Calif.

[21] Appl. No.: 806,424

[22] Filed: Dec. 9, 1985

[51] Int. Cl.$^4$ ............................................. A61L 2/18
[52] U.S. Cl. ...................................... 422/28; 422/292
[58] Field of Search .................... 422/28, 33, 37, 292, 422/295, 300; 134/22.12

[56] References Cited

U.S. PATENT DOCUMENTS

| | | | |
|---|---|---|---|
| 3,779,707 | 12/1973 | Tabone | 422/37 |
| 4,054,998 | 10/1977 | Hesselgren | 422/28 X |
| 4,327,060 | 4/1982 | Nisii | 422/300 |
| 4,362,241 | 12/1982 | Williams | 422/300 X |
| 4,382,788 | 5/1983 | Pelerin | 422/300 X |
| 4,400,357 | 8/1983 | Hohmann | 422/300 X |
| 4,448,750 | 5/1984 | Fuesting | 422/28 X |
| 4,541,992 | 9/1985 | Jerge et al. | 422/300 |
| 4,545,956 | 10/1985 | Ciszewski et al. | 422/28 |
| 4,552,163 | 12/1985 | Biancalana et al. | 422/292 X |

OTHER PUBLICATIONS

Derwent Publications, #15930 E/09.

Primary Examiner—Barry S. Richman
Assistant Examiner—Jill Johnston
Attorney, Agent, or Firm—Morland C. Fischer

[57] ABSTRACT

A compact apparatus and effective method for the cold sterilization and lubrication of a dental handpiece. By virtue of the present invention, a dental handpiece may be sterilized in a relatively short time without exposing the turbine assembly thereof to possible degradation, as has heretofore been caused by conventional methods of sterilization which utilize either high temperature or harmful chemicals. A unique pneumatic pump is described for pumping a supply of liquid sterilant through the interior of the handpiece and past the turbine assembly for destroying harmful bacteria. Next, a supply of water is pumped through the handpiece to flush away any sterilant residue. Lastly, a supply of turbine oil is passed through the handpiece to lubricate the turbine assembly and the components (e.g. bearings) thereof. Therefore, a dental handpiece may be quickly and efficiently sterilized and lubricated, so that a dentist will be more likely to sterilize the handpiece after each use, whereby to prevent the possible spread of disease from one patient to another.

10 Claims, 2 Drawing Sheets

METHOD FOR STERILIZING A DENTAL HANDPIECE

BACKGROUND OF THE INVENTION

1. Field of the Invention

This invention relates to a compact pumping apparatus and to a fast and reliable method for the cold sterilization and lubrication of a dental handpiece.

2. Prior Art

Certain communicable diseases such as, for example, hepatitis, AIDS (acquired immune deficiency syndrome), herpes, and the like, could be inadvertently spread at a dental office when a dental handpiece which has been used in the mouth of an infected patient is later used in the mouths of uninfected patients. Because the dental handpiece is not adequate sterilized or is not at all sterilized after each use, bacteria and other harmful microorganisms may undesirably be transmitted to the mouth of a healthy patient who is treated with the same, contaminated handpiece.

More particularly, a forward spray orifice, common to most conventional dental handpieces, is known to emit an air/water spray or mist in order to cool a work surface within the patient's mouth. When the spray is terminated, an aerosol mixture within the patient's mouth (including saliva, blood and water) is frequently sucked back through the orifice and into the interior of the handpiece. Moreover, bacteria laden aerosol may also be conveyed from an infected patient's mouth to the interior of the handpiece via worm or loose seals at the cutting head of the handpiece. Consequently, in the event that the dental handpiece is not sterilized after each use, a patient in whose mouth the handpiece is later used might become infected with disease, particularly when the handpiece cuts blood vessels during work within such a patient's mouth.

One effective way to sterilize a handpiece is by means of high temperature. In this case, the dentist places the handpiece in an autoclave for approximately 20–45 minutes at a temperature of 300 degrees F. The handpiece must then be cooled down for an additional 3 hours before it is ready for further use. However, such a process of heating and cooling a handpiece is very time consuming and, therefore, requires that the dentist have access to many handpieces with which to treat different ones of his patients. Moreover, heating the handpiece to a high temperature for long periods of time is known to age the seals and damage the bearings of the handpiece turbine assembly, thereby necessitating frequent repair and increased cost. Accordingly, some dentists are reluctant to subject their handpieces to the high temperatures needed to adequately destroy potentially harmful bacteria and microorganisms after each patient has been treated.

Another way to sterilize a handpiece is by means of cold sterilization. In this case, the handpiece is immersed in a reservoir of liquid disinfectant. However, such liquid disinfectant is typically harmful and tends to erode the seals and precision bearings of the internal turbine assembly. What is more, liquid disinfectants frequently leave behind a solid residue which sometimes causes the turbine assembly to become unbalanced, particularly at high speeds of rotation. After continuous out-of-balance rotation, the turbine assembly may fail, thereby also necessitating repair and increased costs. What is still more, the use of a reservoir of liquid disinfectant has generally limited the effectiveness of the cold sterilization process to the exterior of the handpiece. Unfortunately, such a conventional process is not well suited to sterilizing the internal exhaust and intake ports and associated tubing into which disease carrying aerosol may be carried and trapped during the treatment of a contaminated patient.

Consequently, no economic and effective way of internally and externally sterilizing a dental handpiece is known which can be accomplished in a relatively short time without risking degradation to the turbine assembly.

SUMMARY OF THE INVENTION

Briefly, and in general terms, disclosed herein are a gas actuated, pneumatic pumping apparatus and the use of such apparatus in a reliable and relatively quick and economic method for the cold sterilization and lubrication of a dental handpiece. The pneumatic pump includes a hollow, cylindrical housing having pairs of forward and rearward chambers. A double sided actuator assembly extends through the pump housing such that oppositely aligned pistons are adapted for reciprocal movement through respective pairs of the chambers. Intake and outlet lines communicate with each of the forward pair of pump chambers so that supplies of fluid (e.g. a liquid sterilant and water) can be successively pumped from fluid sources, through the ports and associated internal fluid lines of a dental handpiece, and past the turbine assembly thereof by way of the pair of forward chambers. Operation of the pneumatic pump is automatically controlled by a timer controlled solenoid valve which successively provides a supply of gas under pressure to each of the rearward pair of pump chambers for causing the pistons to reciprocate, thereby pumping fluid from the forward pump chambers to the handpiece.

The present method includes the steps of first pumping a supply of liquid sterilant through the interior of the handpiece and past the turbine assembly at the same time that the exterior of the handpiece is soaked in a bath of sterilant. A supply of water is then pumped through the handpiece to flush away any sterilant residue. Finally, a lubricating oil is forced through the handpiece to lubricate the turbine assembly. Thus, the handpiece is lubricated by the same method during which it is also sterilized internally and externally, whereby to minimize maintenance and repair costs to the dentist while preventing the spread of contagious disease by effectively destroying harmful bacteria and microorganisms.

DESCRIPTION OF THE PREFERRED EMBODIMENT

Figure 1:
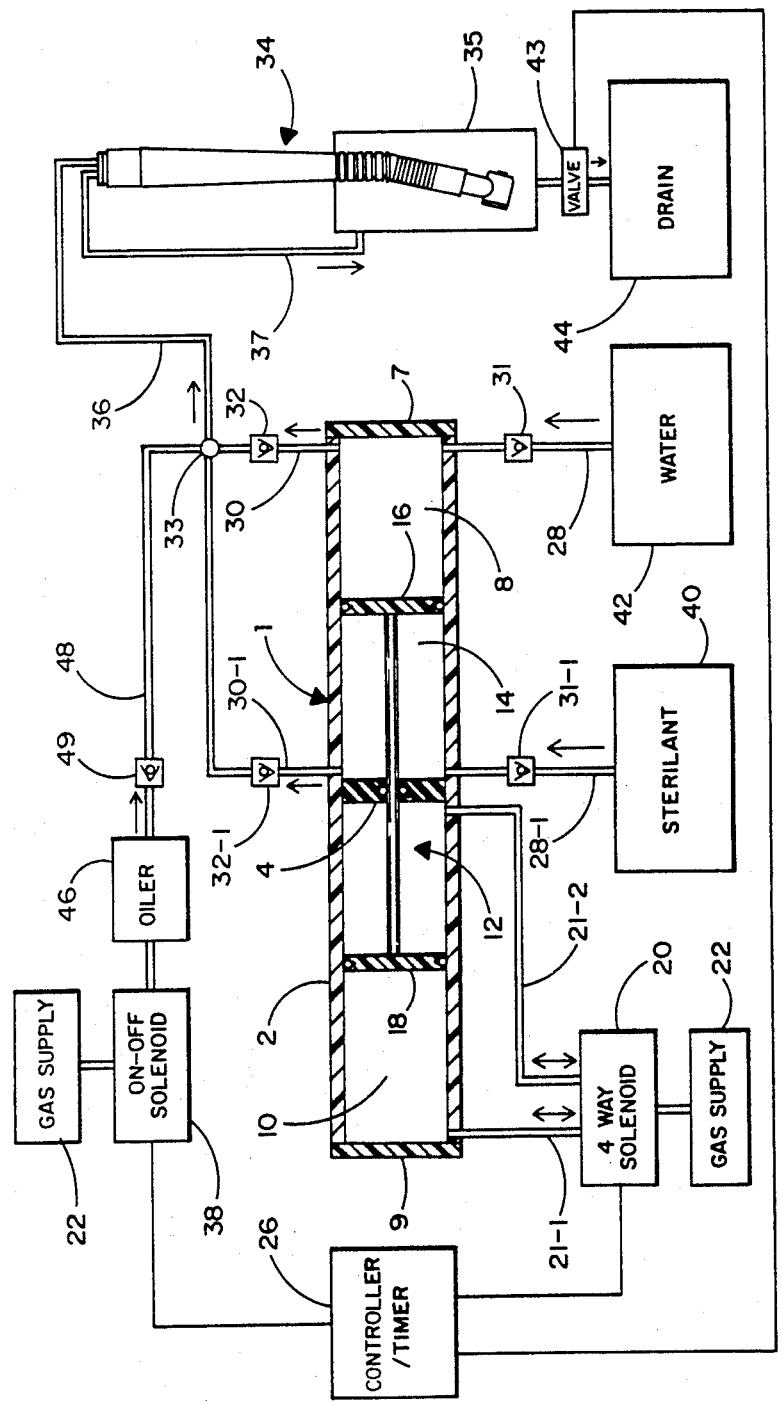
FIG. 1 shows a schematic representation of the pumping apparatus (in cross section) of the present invention interconnected with means for supplying cleaning, sterilizing, and lubricating fluids to a dental handpiece.

The effective method and compact pumping apparatus which form the present invention are now described while referring to FIG. 1 of the drawings. The pumping apparatus is a pneumatic or gas actuated pump 1 having a pump housing 2 which is preferably a hollow, non-corrosive (e.g. plastic) cylinder having a length of approximately 3 to 4 inches and a diameter of approximately 1 to 2 inches. Located within the cylindrical housing 2 is an interior wall 4. Interior wall 4 extends across the pump housing 2, so as to prevent the movement of fluid therepast. The interior wall 4 is spaced approximately midway between a proximal end wall 7 and a distal end wall 9 of housing 2, so that a hollow pump chamber 8 is formed at one side of pump 1 between mid wall 4 and end wall 7, and a hollow pressure chamber 10 is formed at the other side of pump 1 between mid wall 4 and end wall 9.

The interior mid wall 4 has a hole formed therein for slideably receiving therethrough an elongated drive shaft 14 of a double sided actuator assembly 12. One end of the drive shaft 14 terminates at a cylindrical front piston 16. Piston 16 is confined to the pump chamber 8 and is adapted for reciprocal movement through the pump housing 2 between mid wall 4 and the proximal housing end wall 7. The opposite end of drive shaft 14 terminates at a cylindrical rear cylinder 18. Cylinder 18 is confined to the pressure chamber 10 and is adapted for reciprocal movement through the pump housing 2 between the mid wall 4 and the distal housing end wall 9.

A source 22 of gas (e.g. air) under pressure communicates with the pressure chamber 10 in front of and behind the rear piston 18 by way of a 2-position, 4-way solenoid control valve 20 and respective fluid conduits 21-1 and 21-2. By way of example, one such valve which is suitable for use herein is Part No. 8345EL manufactured by Plast-O-Matic Valves, Inc. of Totowa, N.J. The operation of the solenoid control valve 20 for supplying gas to (or venting gas from) chamber 10 via one or the other of the conduits 21-1 or 21-2 is controlled by a controller/timer 26. Controlled timer 26 preferably includes a conventional microelectronic timing chip, such as that manufactured by Motorola Corporation. Depending upon the predetermined cycle of controller/timer 26, the solenoid control valve 20 will permit either the forward or rearward end (relative to piston 18) of pressure chamber 10 to become pressurized with gas supplied from source 22. In the event that the forward end of pressure chamber 10 ahead of piston 18 is pressurized, the actuator assembly 12 will be driven in a rearward direction through pump housing 2 towards distal end wall 9. In the event that the rearward end of pressure chamber 10 behind piston 18 is otherwise pressurized, the actuator assembly 12 will be driven in a forward direction towards proximal end wall 7. The cyclical back-and-forth movement of actuator assembly 12 causes piston 16 to reciprocate through pump chamber 8 for a purpose which will now be described.

Communicating with the pump chamber 8 in front of the forward piston 16 by way of a fluid intake line 28 and an associated check valve 31 is a containment vessel 42 holding a supply of water. Also communicating with the forward end of chamber 8 is a fluid outlet line 30 and an associated check valve 32. Communicating with the pump chamber 8 behind the forward piston 16 by way of another fluid intake line 28-1 and an associated check valve 31-1 is a containment vessel 40 holding a supply of liquid sterilant. Also communicating with the rearward end of pump chamber 8 is another fluid outlet line 30-1 and an associated check valve 32-1. In this manner, water may be sucked from containment vessel 42 into the pump chamber 8 between piston 16 and the proximal end wall 7 of housing 2 when the actuator assembly 12 is moved in a rearward direction towards distal end wall 9. Water will be pumped from chamber 8 into fluid outlet line 30 when the actuator assembly 12 is moved in a forward direction towards proximal end wall 7. Similarly, sterilant may be sucked from containment vessel 40 into pump chamber 8 between piston 16 and mid wall 4 when the actuator assembly 12 is moved in its forward direction. Sterilant will be pumped from chamber 8 into outlet line when the actuator assembly 12 is moved in its rearward direction.

Accordingly, the reciprocating movement of actuator assembly 12 through housing 2 alternately pumps water and disinfectant from containment vessels 42 and 40 into fluid outlet lines 30 and 30-1, respectively, depending upon the direction in which piston 16 moves through pump chamber 8. Each of the fluid outlet lines 30 and 30-1 is interconnecte with a common coupling 33, so that the water and sterilant can be supplied to a dental handpiece for quickly and reliably cleaning and sterilizing such handpiece.

In order that the turbine assembly of a dental handpiece may also be lubricated, a (low volume, low pressure) oiler 46 containing a supply of turbine oil, or the like, is interconnected with coupling 33 by way of an oil line 48 and an associated check valve 49. The aforementioned source 22 of gas (i.e. air) under pressure is connected to oil line 48 by way of an ON-OFF solenoid valve 38. The operation of solenoid valve 38 is controlled by controller/timer 26. Thus, and as will soon be described in greater detail, depending upon the predetermined cycle of controller/timer 26, pressurized gas or oil may be supplied to the handpiece via oil line 48 so as to purge the internal fluid lines or lubricate the turbine assembly.

The method for utilizing the pneumatic pump 1 of FIG. 1 to sterilize and lubricate a dental handpiece 34 is now disclosed. The handpiece 34 is laid in an empty fluid reservoir 35. The reservoir 35 is interfaced with a fluid drain 44 by way of a conventional fluid valve 43. The opening and closing of valve 43 is controlled by the aforementioned controller/timer 26. Therefore, depending upon the predetermined cycle of controller/timer 26, the valve 43 may be periodically opened, so that fluid received with the reservoir 35 may be drained therefrom (e.g. under the influence of gravity) and discarded at drain 44. The exhaust port 36 of handpiece 34 is connected to coupling 33 so as to be capable of receiving one or another of the fluids being supplied through outlet lines 30 and 30-1 and oil line 48. The intake port 37 of handpiece 34 is interfaced with reservoir 35, so that fluids which pass through the interior of handpiece 34 may be supplied to and collected by reservoir 35.

During a sterilizing step of the present method, the containment vessels 40 and 42 are filled with liquid sterilant and water, respectively, so that the rearward side (relative to piston 16) of the pump chamber 8 of pneumatic pump 1 is connected to receive sterilant and the forward side of pump chamber 8 is connected to receive water. The liquid sterilant of containment vessel 40 may be any commercially available cold sterilant. However, in accordance with a preferred embodiment of this invention, one suitable sterilant for use herein is a non-glutaraldehyde cold sterilant manufactured by Alcide Corporation of Norwalk, Conn. and known commercially as EXSPOR.

The pneumatic pump 1 is activated (by means of controller/timer 26 and solenoid valve 20) in the manner previously described to cause piston 16 to move in a rearward direction and thereby pump sterilant from pump chamber 8 through the exhaust port 36 and the air and water lines (not shown) of handpiece 34 by way of outlet line 30-1. The sterilant passes through the interior of handpiece 34 and around the turbine assembly. The sterilant then exits the handpiece 34 at the intake port 37 and the forward spray orifice (also not shown), such that excess sterilant fills the reservoir 35 and covers the handpiece 34. Inasmuch as the handpiece 34 is immersed in a sterilant bath within the reservoir 35 and sterilant is also passed through the ports and associated fluid lines, the handpiece wil be sterilized both internally and externally without use of harmful chemicals or time consuming and possibly degrading high temperatures. The handpiece is permitted to soak in sterilant for a suitable time (e.g. from 1 to 3 minutes) needed to destroy harmful bacteria and microorganisms. The sterilant is emptied from reservoir 35 by way of valve 43 and discarded at drain 44.

During a flushing step of the present method, water from containment vessel 42 (which has filled the forward side of pump chamber 8 during the rearward movement of piston 16) is pumped into and through the exhaust port 36 and the water and air lines of handpiece 34 by way of outlet line 30. That is, the controller/timer 26 operates solenoid valve 20 so that gas under pressure is vented from the forward side of pressure chamber 10 (via conduit 21-2) at the same time that gas is supplied to a rearward side of pressure chamber 10 (via conduit 21-1) for causing the movement of pistons 16 and 18 in a forward direction towards proximal end wall 7. Like the passage of sterilant during the preceding sterilization step, the water is pumped through the interior of handpiece 36, around the turbine assembly, and out the intake port 37 and forward spray orifice for collection in reservoir 35 and disposal at drain 44. Controller/timer 26 is programmed so that the flushing step takes approximately 15 to 30 seconds. Accordingly, the ports and associated fluid lines of handpiece 34 are flushed with water, so as to remove any sterilant residue and thereby prevent the turbine assembly from going out of balance, as might otherwise be caused by a buildup of solidified sterilant.

Purging and lubricating steps follow the flushing step. More particularly, the controller/timer 26 opens solenoid valve 38 to permit gas (i.e. air) from source 22 to be supplied under relatively low (e.g. 5 pounds of) pressure to the exhaust port 36 of handpiece 35 by way of oil line 48. The gas dries the handpiece 35 by purging excess water from the interior thereof via intake port 37 and the forward spray orifice.

Following the purging step, a few drops of turbine oil are supplied, under pressure, from oiler 46 to exhaust port 36 by way of oil line 48. The turbine oil is supplied to the interior of handpiece 34 for approximately 30 seconds (e.g. at 5 pounds of pressure) with the turbine assembly rotating normally. In this manner, the turbine assembly can be periodically lubricated and properly maintained during each time that the handpiece is sterilized. Finally, the aforementioned purging step may be repeated with relatively low pressure gas so as to purge the interior of handpiece 34 of excess oil which may remain upon completion of the lubricating step.

Figure 2:
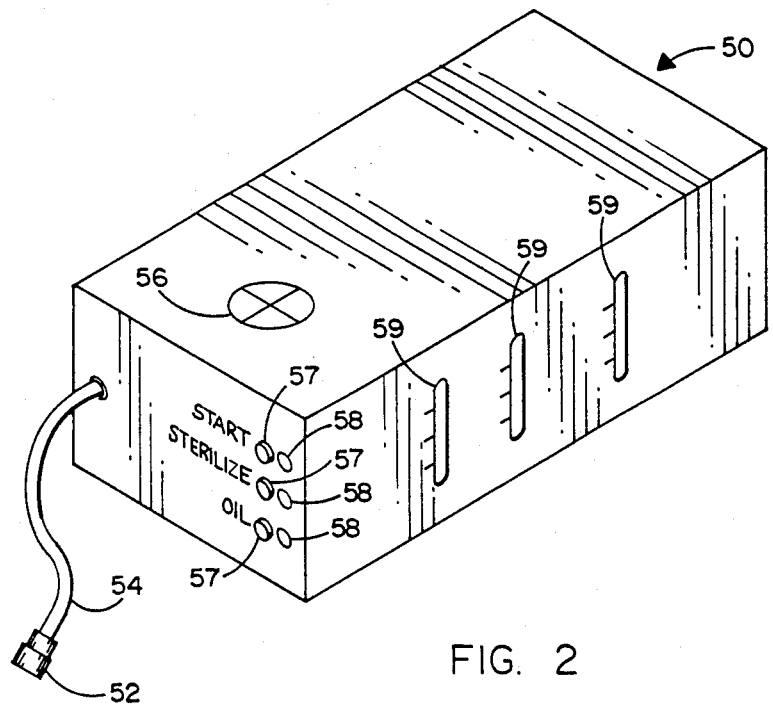
FIG. 2 shows one example of an enclosure to which a dental handpiece may be connected so as to be automatically sterilized and lubricated according to the present method.
Figure 3:
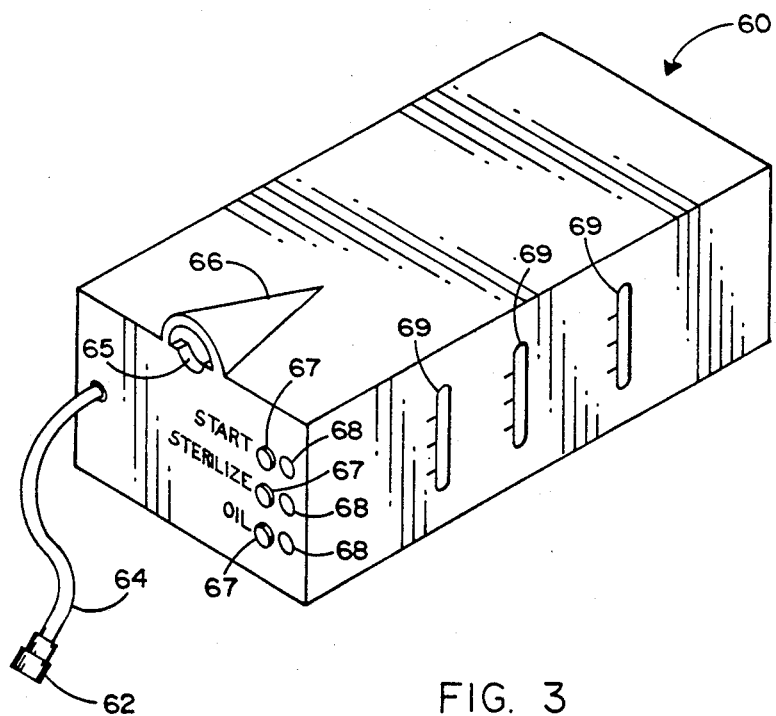
FIG. 3 shows another example of an enclosure to which a dental handpiece may be connected so as to be automatically sterilized and lubricated according to the present method.

FIGS. 2 and 3 of the drawings show enclosures 50 and 60 which can house the fluid pump 1 and associated containment vessels 40 and 42 and drain 44 of FIG. 1 to facilitate the automatic sterilizing and lubricating of a dental handpiece. Referring first to FIG. 2, the enclosure 50 may be formed from a suitable material, such as plastic. Extending outwardly from enclosure 50 is a fluid conduit 54 having a coupling 52 connected at a terminal end thereof. A dental handpiece (not shown) may be connected to coupling 52 in the same manner that the handpiece 34 of FIG. 1 is connected to coupling 33. A removable cover section 56 in the top of enclosure 50 is removed so that the handpiece may be located in a fluid reservoir (35 of FIG. 1) at the interior of enclosure 50. At one side of enclosure 50 are a plurality of push buttons 57 and associated indicator lights 58. An operator may depress a push button 57 designated START to automatically complete a full cycle of operation for sterilizing and lubricating a handpiece in accordance with the present method. To selectively initiate only a sterilizing or lubricating step of the present method, the operator may push a particular one of the other push buttons 57 designated STERILIZE or OIL. Indicator lights 58 indicate which of the push buttons and steps of the present method have been selected. Transparent windows 59 are formed through a face of enclosure 50. The windows 59 are arranged in proximity to the sterilant and water containment vessels 40 and 42 and drain 44, so that the operator may easily visualize the fluid levels in such vessels and drain and thereby ascertain whether to add or to discard fluid therefrom. In addition, limit switches may be associated with the containment vessels 40 and 42 and drain 44, so as to prevent operation in the event of an approaching fluid shortage or overflow.

FIG. 3 shows another enclosure 60 having a fluid conduit 64 extending therefrom with a coupling 62 connected at a terminal end thereof. An access opening 65 is formed through a side of enclosure 60 with a conical guide 66 formed thereover. With a handpiece connected to conduit 64 at coupling 62, the handpiece may be inserted through access opening 65 and located in a fluid reservoir within enclosure 60. A plurality of push buttons 67 and associated indicator lights 68 are located at a side of enclosure 60. Transparent windows 69 are formed through a face of enclosure 60. The function and operation of buttons 67, lights 68, and windows 69 are identical to that previously described when referring to FIG. 2 and, therefore, will not be again described.

By virtue of the present invention, a compact pneumatic pump and effective method is available for the cold sterilization and lubrication of a handpiece. The present method is substantially automatic and permits the handpiece to be easily lubricated at the same time that it is sterilized both internally and externally. Because of the reliable and relatively fast (e.g. approximately 5 minutes) as herein disclosed, a dentist will be more likely to sterilize all of his handpieces after each use, so as to advantageously prevent the spread of contagious disease at the dentist's office. Moreover, the present method permits the turbine assembly of the handpiece to be regularly lubricated, so that time lost for maintenance and costs due to repair can be minimized.

It will be apparent that while a preferred embodiment of the present invention has been shown and described, various modifications and changes may be made without departing from the true spirit and scope of the invention.

Having thus set forth a preferred embodiment of the present invention, what is claimed is:

1. A method for simultaneously cold sterilizing the interior and exterior of a dental handpiece and a turbine assembly within said handpiece, said method including the steps of:

pumping a fluid sterilant into either one of a fluid intake port or a fluid exhaust port of said dental handpiece, through the turbine assembly at the interior of said dental handpiece, and out the other one of said fluid intake port or said fluid exhaust port for sterilizing the interior of said dental handpiece;

locating said dental handpiece in a reservoir and collecting in said reservoir excess sterilant which is discharged from said fluid intake port or exhaust port, and soaking said dental handpiece in a bath of sterilant within said reservoir for sterilizing the exterior of said dental handpiece; and pumping a sterilant removing fluid into either one of said fluid intake port or said fluid exhaust port of said dental handpiece, past the turbine assembly, and out the other one of said ports for removing any sterilant residue from the interior of said dental handpiece.

2. The method recited in claim 1, including the additional step of blowing a gas into one of said fluid intake port and said fluid exhaust port of said dental handpiece, past the turbine assembly and out of the other of said fluid intake port and said fluid exhaust port for purging the sterilant removing fluid from the interior of said dental handpiece and thereby drying said interior.

3. The method recited in claim 1, including the additional step of supplying a lubricating fluid into one of said fluid intake port and said fluid exhaust port of said dental handpiece, past the turbine assembly and out of the other of said fluid intake port and said fluid exhaust port for lubricating said turbine assembly.

4. The method recited in claim 3, including the additional step of blowing a gas into one of said fluid intake port and said fluid exhaust port, past the turbine assembly and out the other of said fluid intake port and said fluid exhaust port for purging excess lubricating fluid from the interior of said dental handpiece.

5. The method recited in claim 1, including the additional steps of supply the fluid sterilant by means of a pump, and surrounding said pump and said reservoir by a common enclosure.

6. The method recited in claim 5, including the additional steps of forming an opening in said enclosure and extending at least part of said dental handpiece through said opening, so that at least a cutting head of said dental handpiece is received in said reservoir.

7. The method recited in claim 1, including the additional steps of pumping the fluid sterilant by means of a pressure actuated pump having at least first and second noncommunicating pump chambers, connecting a first of said pump chambers between a source of said fluid sterilant and one of said fluid intake port and said fluid exhaust port, and connecting of second the said pump chambers between a source of water and one of said fluid intake port and said fluid exhaust port.

8. The method recited in claim 7, including the additional step of pumping sterilant outwardly from said first of said pump chambers to one of said fluid intake port and said fluid exhaust port while drawing water inwardly to said second of said pump chambers from said water source.

9. The method recited in claim 8, including the additional step of pumping water outwardly from said second of said pump chambers to one of said fluid intake port and said fluid exhaust port while drawing fluid sterilant inwardly to said first of said pump chambers from said fluid sterilant source.

10. The method recited in claim 9, wherein said pump also has first and second noncommunicating pressure chambers connected to a source of gas under pressure and the method includes the additional steps of:

filling said first of said pressure chambers with gas from said source while venting said second of said pressure chambers to the atmosphere for causing fluid sterilant to be pumped outwardly from said first of said pump chambers and water to be drawn into said second of said pump chambers, and filling said second of said pressure chambers with gas from said source while venting said first of said pressure chambers to the atmosphere for causing water to be pumped outwardly from said second of said pump chambers and fluid sterilant to be drawn into said first of said pump chambers.

* * * * *